United States Patent [19]

Lersmacher et al.

[11] 4,204,769
[45] May 27, 1980

[54] CUVETTE FOR FLAMELESS ATOM ABSORPTION SPECTROSCOPY

[75] Inventors: Bernhard Lersmacher, Aachen; Hans Lydtin, Stolberg; Karlheinz Schelhas, Aachen, all of Fed. Rep. of Germany; Wilhelmus F. Knippenberg, Eindhoven, Netherlands

[73] Assignee: U.S. Philips Corporation, New York, N.Y.

[21] Appl. No.: 870,200

[22] Filed: Jan. 17, 1978

[30] Foreign Application Priority Data

Jan. 20, 1977 [DE] Fed. Rep. of Germany ....... 2702189

[51] Int. Cl.² ........................................... G01N 21/16
[52] U.S. Cl. .................................... 356/244; 356/312
[58] Field of Search ................................. 356/244, 312

[56] References Cited

U.S. PATENT DOCUMENTS

| 3,788,752 | 1/1974 | Slavin et al. | 356/244 X |
| 3,979,162 | 9/1976 | George | 356/244 X |
| 4,111,563 | 9/1978 | Tamm | 356/312 X |

*Primary Examiner*—John K. Corbin
*Assistant Examiner*—Matthew W. Koren
*Attorney, Agent, or Firm*—Thomas A. Briody; Jack Oisher; Paul R. Miller

[57] ABSTRACT

Cuvettes of carbonized laminated fabric with a surface layer of pyrolytic graphite are easy to manufacture, have a high mechanical rigidity and no memory effect and enable the operation of analysis apparatuses at normal mains voltage (220 V).

8 Claims, 4 Drawing Figures

CUVETTE FOR FLAMELESS ATOM ABSORPTION SPECTROSCOPY

The invention relates to a cuvette for flameless atom absorption spectroscopy (AAS) which consists of a carbon-containing material.

Such cuvettes serve as a receptacle and heating device for a probe to be analysed; and constitute an essential part of apparatuses for the AAS. The cuvettes are preferably used are tubular elements having a more or less complicated geometrical shape (German Offenlegungsschrift No. 20 06 032, German Offenlegungsschrift No. 21 48 777), and cuvettes generally consist of highly temperature-resistent electrically conductive material since heating of the probe to be analyzed usually occurs by resistance heating of the cuvettes with direct current. Of course, other types of heating, for example, inductive heating or heating by radiation, are alternatively possible.

The material preferred for such cuvettes is carbon, in particular in the form of spectrum graphites which satisfy nearly all of the imposed requirements in a substantially ideal manner. Only their comparatively low mechanical rigidity as well as a certain porosity are disadvantages. In order to compensate for low mechanical rigidity, the cuvettes have to be manufactured with rather thick walls, for example in an order of magnitude of 1 mm. However, due to the low electrical resistance of large wall thicknesses they require a high energy, or high currents. This means that expensive electrical supply units are necessary for heating. The porosity of the graphites results in the analysis substance easily penetrating into the walls of the cuvette and, when the cuvette is used again, a residual substance of one analysis may influence the result of the subsequent analyses. This effect will hereinafter be termed "memory effect" which is to be understood to mean a secondary effect and superposition effect in the sense of an adulterating influence of a substance from a preceding analyses retained in the pores of the cuvette on the result of the succeeding analysis.

In order to reduce or compensate for the above described disadvantages, several proposals have been made. For example, the use of glassy carbon (British Pat. No. 13 23 100) provides a dense, mechanically rigid material having an increased specific electric resistance—and hence a lower amount of energy, reduced wall thickness, and lower memory effect. Apparently, this type of cuvette has not been acceptable. The reasons therefor might be:

1. The rigidity and impermeability of glassy carbon is reduced at high temperatures (in AAS temperatures up to 3000° C. are reached).
2. The manufacture of molded parts, in particular the manufacture true to size of cuvettes of solid glassy carbon, is comparatively expensive because of long carbonisation times and expensive aftertreatment (for example grinding with a diamond tool) and is generally too expensive for mass produced articles such as these cuvettes.

At present, substantially only cuvettes of spectrum graphite are used in AAS. A substantial improvement of spectrum graphite in regard to the suppression of the memory effect can be achieved by coating with a thin layer of pyrolytic graphite (for example, in a thickness of approximately 10 $\mu$m). In addition it is to be noted that according to another basic known conception, for example, set forth in German Offenlegungsschrift No. 22 25 421, porous carbons, such as foam carbon or carbon fabrics, have been proposed as materials for probe supports and heating elements in AAS. However, the use of such materials requires a completely different analysis apparatus, as well as a different measuring method which is not presently used. The method substantially used today only in the AAS is based on apparatus comprising the above-described cuvettes.

It is the object of the invention to provide a cuvette which can easily be manufactured, has a large mechanical rigidity and has no memory effect.

According to the invention, this object is achieved with a cuvette of the kind mentioned in the preamble in that the cuvette consists of a basic carbon body and a carbon layer present thereon with the material of the basic body being manufactured by carbonization of laminated fabric using a thermosetting resin, such as phenol resin or cresol resin, and cotton fabric.

A method of manufacturing carbon bodies which can be used according to the invention, in which such laminated fabrics are carbonized is proposed in Patent Application No. P 26 48 900.9. Carbonisation is to be understood to mean a heating of the laminated fabric in a non-oxidizing atmosphere at a temperature above 800° C. For further details of the manufacture and the properties of the materials used for the device according to the invention reference is made to the above-mentioned patent application, which is set forth inafter.

The invention relates to a method of manufacturing carbon bodies in which bodies which consist of flat or curved sheets consisting of several layers of mainly cellulose packed or wound one on the other and impregnated with a curable polymeric material cured under pressure, are heated to a non-oxidizing atmosphere at a temperature >800° C.

The carbon bodies manufactured in this manner are suitable inter alia for heating tubes for spirals for resistance-heated furnaces, for melting-crucibles and boats, for example, for melting chemically aggressive materials, as well as for pipes and plates for lining containers and apparatuses.

In a method described in German Offenlegungsschrift No. 21 04 680 are used as sheets consisting mainly of cellulose: cardboard, pasteboard, chipboard and plywood plates, for example, plates of filter cardboard or cardboard pipes. When cardboard or pasteboard is used, the steps in the manufacture prior to the carbonization correspond substantially to the known method of manufacturing hardpaper, with the remarkable difference that in curing a comparatively low pressure of approximately 1 to 30 kp/cm$^2$ is used. In the conventional manufacture of hardpaper, pressures during hardening of 100 kg/cm$^2$ and more are usual. Furthermore, according to German Offenlegungsschrift No. 21 04 680 particularly highly resinous starting materials are used (resin content approximately 400% by weigth), whereas the resin part in commercial hardpaper is 30 to 50% by weight.

When bodies of commercial hard paper consisting of several layers of phenol resinimpregnated paper hardened under pressure or similar cardboard, are heated in a nonoxidizing atmosphere at the rate of approximately 5° to 10° C. at 800° to 1200° C. as described in German Offenlegungsschrift No.21 04 680, the bodies swell interlaminarly and are substantially useless.

It is an object of the invention or produce thickwalled parts with a defined microporosity without the swelling up occurring.

According to the invention, this object is achieved by a method of the kind mentioned in the preamble in which hard fabric on the basis of phenol resin or cresol resin and cotton fabric are heated.

In the starting material for the method according to the invention commercial products are preferably used which are described, for example, in Saechtling-Zebrowski "Kunststoff-Taschenbuch" 19$^{th}$ed, Munich-Vienna 1974, pages 417 to 419 and table 76. Of course it is also possible that, if necessary, hard fabric bodies having a non-commercial composition are manufactured. It is surprising that the swelling up observed in the carbonization of hard paper does not occur in the carbonization of hard fabric when hard paper and hard fabric are combined under the common nomination "laminated pressed materials" ("Kunststoff-Taschenbuch" as above).

As a starting material for the method according to the invention a certain group of laminated pressed materials are thus used, namely hard fabric, which mainly consists of phenol resins or cresol resins reinforced with cotton fabric. In accordance with the resin constituents and fabric constituents and according to the type of resin and fabric fineness, commercial hard fabrics are available of differing properties and qualities (see, for example, "Kunstsoff-Taschenbuch" as above). Hard fabrics are available both as laminated pressed materials in the form of plates and as wound laminates in the form of rods and pipes. So the starting material is a bonding material which consists essentially of a phenol resin matric reinforced with cotton fabrics. Such a bonding material may also be referred to as "phenol resin laminate".

During the further examination it has been found that especially commercial hard fabrics often show more or less strong inhomogeneties in their construction. These are preferably characterized by areas of larger or smaller resin content. They can be produced at will in that, for example, during the manufacture of laminated compressed plates the upper and/or lower fabric layer (cover layer) is impregnated more strongly with resin than the remaining (inner) layers so as to obtain in this manner a smooth, dense, so in general a better, for example better-looking surface. Another inadvertent inhomogeneity creeps into the starting material in that the fabric layers impregnated or to be impregnated themselves are defective, are pleated and locally show considerably different resin impregnations. These inhomogeneities resulting from the manufacture are hereinafter referred to as "resin nests". The ratios described on the inhomogeneity as a result of locally increased resin concentrations in the starting material for the manufacture and the properties of the carbon material according to the invention have important consequences. Inter alia the speed of the carbonization also depends on the fact whether a starting material is available having dense cover layers, that it highly resinous layers, or whether stronger resin nests occur in the material. Although in general the heating rates described below apply, but in each case the presence of inhomogeneities of the described nature are to be considered.

The heating, that is the carboniation, of the hard fabric bodies is preferably carried out as follows: first the bodies are heated in a nitrogen atmosphere or in a vacuum at a rate between 1° C./h and 50° C./h to 800° C., then cooled to room temperature in 1 to 10 hours and then heated in a vacuum of $10^{-1}$ to $10^{-3}$ mm Hg at at least 1600° C. in 1 to 10 hours. It is to be noted that the heating and cooling rates to be chosen within the above given ranges depend on the wall thickness of the bodies and that in that sense that larger wall thicknesses require lower rates.

When the starting material used according to the invention is subjected to such a defined temperature-time treatment in an inert atmosphere or in a vacuum, a product which consists for the greater part of elementary carbon is obtained after reaching a temperature of at least 800° C. and subsequent cooling. An after-treatment to 1400° C., in some cases also to 2000° C. and higher, in a vacuum (approximately $10^{-3}$ mm Hg) has for its result that impurities, in particular also residual hydrogen, are expelled.

From the process in the solid state pyrolysis it is known that the volatile pyrolysis products formed during thermal decomposition must leave the treated body via diffusion processes. In manufacture of glassy carbon it is a volume diffusion in which the outdiffusion of the decomposition products occurs particularly slowly. This means that, for example, with wall thicknesses of the starting material of approximately 5 mm, carbonization times of several 100 hours up to 1000 hours are necessary. So for practical purposes this results in a maximum layer thickness of glassy carbon of approximately 3 mm.

It has now surprisingly been found that in the phenol resin laminates used according to the invention the carbonization can be carried out much more rapidly, although said starting material with specific weights of 1.3 to 1.4 g cm$^{-3}$ and fully dense packing should be comparable to unfilled phenol resins. The strongly deviating carbonization behavior can be explained as follows. When the pyrolytic decomposition sets in after reaching a temperature of approximately 280° to 300° C., the out-diffusion of the decomposition products from the phenol resin is considerably favored along the embedded fabric threads. This type of surface diffusion will vary rapidly increase in intensity since the cotton decomposes comparatively more strongly (higher loss of weight than phenol resin) and as a result of this regular channels are formed. The initial volume and grain limit diffusion changes into the "rapid" pore diffusion at a very early instant, that is at the beginning of the thermal decomposition. The practical meaning of this pyrolysis mechanism resides in the fact that pyrolysis cycles and aftertreatment cycles can now be made much shorter or, which is actually the same, that very much larger wall thicknesses are possible. For example the carbonization cycle for a material having a wall thickness of 100 mm requires approximately the same time as the preparation of a piece of "solid" vitreous carbon of 3 mm wall thickness.

In the product of the method according to the invention it deals with a fine-porous carbon body having the crystalline or paracrystalline habit of vitreous carbon. This new material is the product of a solid state pyrolysis.

Closer examination of the final product proves that a carbon body having very fine regular pores has been formed. Besides this "primary" porosity there is a "secondary" porosity which is determined by the fibrilar fine structure of the fabric embedding. The qualitatively described performance of the diffusion allows the conclusion that even larger wall thicknesses than the said 100 mm can be carbonized in reasonable times.

A rough calculation proves that the volume of a "primary" individual pore is of the order of magnitude of $10^{-6}$ cm$^3$. In the carbonization of the new material up to 1600° C. a linear shrinkage occurs of 20 to 30%. The loss of weight occurred in this range lies at 60 to 65%. With the shrinkage and weight loss values correspond specific weights of the final product of approximately 1.00 to 1.40 g cm$^{-3}$. These are approximately 45 to 60% of the theoretical density of graphite. The overall pore volume thus is 40 to 55%. With the above-indicated value for the volume of a "primary" individual pore corresponds an average pore number per unit by volume of approximately $0.5 \cdot 10^6$ pores/cm$^3$.

The last-mentioned values characterize the new material in a characteristic manner. It closes in a way the gap between the known macroporous foam (vitreous carbon foam, see for example German Offenlegungsschrift No. 24 53 204) with densities of 0.1 to 1.0 g cm$^{-3}$ and the solid vitreous carbon with densities of 1.45 to 1.55 g cm$^{-3}$.

X ray analytic investigations prove that the new material is "amorphous" and paracrystalline, respectively, as vitreous carbon up to treatment temperatures of 2300° C. Consequently, its hardness, resistance to detrition and mechanical rigidity is also comparatively high (resistance to pressure $\geq 10^4$ N/cm$^2$). The coefficient of the heat conductivity lies at 1 to $3.10^{-2}$cal grd$^{-1}$cm$^{-1}$s$^{-1}$, the specific electrical resistance at 1.2 to 1.6 $10^{-2}$ $\Omega$cm.

In particular the above surface and cover layers, respectively, have a considerable influence on a series of physical properties. In general they produce larger surface hardnesses, rigidities, and so on in the carbonized material. Particularly strong is also the influence on the permeability of the material for liquids and gases. For example, in measurement of materials having a "dense" surface, permeability coefficients for air were found of $10^{-3}$ to $10^{-4}$ cm$^2$/s. The permeability increases approximately by a factor 100 to $10^{-2}$ to $10^{-4}$ cm$^2$/s only by grinding off.

It was furthermore found that it is advantageous to consider already in the mechanical working of the moulded body of laminated fabric the anisotropy "impressed" in the basic material. For example, a tubular or cylindrical body will behave differently both during the carbonization (more favourable heating rates are possible) and in the carbonized final condition have different properties in accordance with the fact whether it has been worked out of the laminated compressed material with its cylinder axis at right angles to, parallel to or in undefined position to the lamination. The consideration of this anisotropy which is natural to the material can be used optimum in the preparation, in accordance with the use, both as regards the properties and also as regards the carbonization behaviour. So advantageously bodies will be worked from the hard fabric prior to heating in such manner that the position of the fabric layers inside the bodies is matched to the desired properties of the carbon bodies.

The advantage of the method according to the invention is that an easily available, because commercially available, starting material may be used. Another advantage is that very thick-walled parts can be manufactured by it. On the other hand, due to the high mechanical rigidity, the manufacture of very thin-walled parts is possible. The raw material can very easily be worked by free-cutting machining. For the carbonized material a working with a hard material tool is possible to a limited extent. Preparatory treatments, for example as in the manufacture of the glassy carbon foam, are not necessary.

Application possibilities for the carbon-carbon material manufactured according to the invention are, for example:

(a) crucible and container material due to the chemical inactivity and high resistance to detrition as an alternative for graphite crucibles.

(b) Heat conductors due to the comparatively high specific resistance.

(c) High temperature resistant heat insulation due to low specific heat conductivity.

(d) Mechanically stable construction material of low specific weight.

(e) Prothesis material for the veterinary and human medicine due to the immune biological indifference against fabric.

(f) Fine-porous corrosion resistant filters for liquids and gases (acids and vapours)

(g) Electrodes

The invention will be described in greater detail with reference to a drawing and a few examples.

In the drawing

Figure 3:
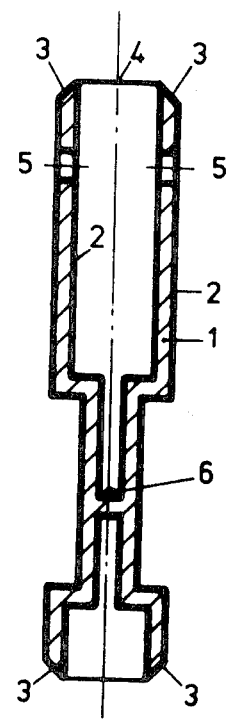

FIG. 3 shows a raster electron microscopic photograph of the carbon-bonding material manufactured according to the invention, magnification approximately 55 fold, FIG. 4 shows a diagram in which temperature-time cycles of a carbonization are shown diagrammatically of a 15 mm thick hard fabric plate, FIG. 5 shows a diagram in which the dependence of the heating rate on the shortest diffusion path (=half wall thickness) is plotted.

Figure 1A:
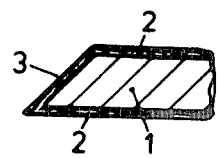
FIGS. 1a, 1b and 1c show bodies of the starting material to be carbonized.

FIG. 1a shows a solid bar and FIG. 1b shows a tube of wound hard fabric, FIG. 1c shows a plate of laminated compressed material.

It is shown in FIGS. 2a and 2b by broken lines how a body 1 to be carbonized can be worked from a block 2 of laminated compressed material, for example, by punching, cutting, sawing or milling, the axis of symmetry 3 of the body being at right angles to the lamination of the laminated compressed material in FIG. 2a and parallel in FIG. 2b.

The structure of the original cotton fabric is still visible in FIG. 3. The photograph shows that the material manufactured according to the invention is a bonded body.

In FIG. 4, the temperature $\theta$ in °C. is ploted against time t in hours. 4 denoted a carbonization cycle in an inert gas, for example nitrogen, and 5 denotes an after-treatment cycle (for cleaning) in a vacuum.

With reference to FIG. 5, first the expression "shortest diffusion path" is explained as follows: in bodies of high symmetry, so balls, cubes, cylinders, parallelepiped-shaped plates, and so on, generally that geometric dimension is decisive of the progress of the diffusion process which describes the shortest distance from a point situated in the center of the given body to the surface. For example, in the case of a wire this is half the wire diameter, in a plate half the plate thickness, etc. The longer said characteristic path, the slower should the temperature increase during the carbonization be carried out.

In FIG. 5 the shaded surface shows the range of the heating rate $\Delta\theta/\Delta t$ as a function of the shortest diffusion path $\delta$ (in mm). The variation width denoted by the shaded area comprises approximately all commercial starting materials.

EXAMPLE 1

For the manufacture of an acid-proof filter disk, a circular disk of 80 mm diameter is manufactured from a hard fabric plate of 10 mm thickness by sawing and turning. The more highly-resinous cover layers of the starting material are removed by turning-off a layer of 1 mm thickness. The resulting circular body of approximately 8 mm thickness is then degreased in a solvent, for example ethanol/acetone.

The carbonization is then carried out. In a first carbonization cycle the body is heated to a temperature of 800° C. in a nitrogen atmosphere at a rate of approximately 4° per hour and then cooled to room temperature within 3 to 4 hours. The body now already has essentially the desired shape and properties. In order to remove residual ilmpurities as well as for stabilization of the resulting carbon body, a second temperature treatment in a vacuum is carried out. For this purpose, the body is heated to a temperature of 1600° C. in a vacuum furnace at a pressure of approximately $10^{-3}$ mm Hg within 20 hours and then cooled to room temperature in 16 hours.

The final product is a microporous disk having a density of 1.15 g cm$^{-3}$. The thickness is 7.8 mm, the diameter 60 mm. The permeability for air was determined at approximately 5.10 cm$^2$/s.

EXAMPLE 2

For the manufacture of a heat conductor from the material according to the invention a meander-shaped body having an overall length of 1250 mm and a pitch width of 10 mm is worked by sawing and milling from a 5 mm thick hard fabric plate. The said meander is then subjected to the carbonization and after-treatment cycles as described in example 1. However, the carbonization was carried out with a temperature increase of 10° C./h up to 800° C., the after-treatment with 100° C./h up to 1600° C.

The final product is a meander of detrition-resistant, porous carbon which has experienced in the longitudinal dimensions a linear shrinkage of approximately 28%, in the thickness, that is at right angles to the lamination, a shrinkage of 20%. The electrical resistance per cm length is approximately 0.0.3Ω with an overall resistance of 2.8Ω. (Resistance elements up to approximately 15Ω were manufactured in the same manner by corresponding proportioning.

EXAMPLE 3

From a solid rod of 100 mm diameter of wound hard fabric, a crucible was manufactured by turning and grinding. The raw crucible had an outside diameter of 95 mm, an inside diameter of 81 mm, a wall thickness of 7 mm and a bottom thickness of 10 mm with an outside height of 140 mm. The carbonization was carried out by heating at 800° C. in 150 hours, the after-treatment by heating in a vacuum of $10^{-3}$ to $10^{-2}$ mm Hg to 1600° C. in 24 hours.

The final product obtained was a microporous carbon crucible whose dimensions—approximately 75 mm outside diamter, 63 mm inside diameter, inside height 103 mm and overall height 110 mm—correspond to a linear shrinkage of 21 to 22%. The density of the crucible material is 1.12 g cm$^{-3}$.

EXAMPLE 4

Rods of hard fabric having dimensions 4.4.66 mm$^3$ were heated in flowing nitrogen in a heating-cooling cycle with linear temporal temperature variation at differently high temperatures. In the region of the transition "polymer→carbon" a particularly strong change of the resistance occurs in the temperature range of 500° to 700° C. (for the variation of the specific resistance as a function of the treatment temperature of glassy carbon, see picture 5 in Chemie Ing. Techn. 42 (1970) No. 9/10, pp. 659–669). It is thus possible, by directed partial carbonization, to manufacture test resistors approximately in the range of 100 MΩ to 1Ω and smaller. For the rods of the above given dimensions, resistors between 5 MΩ and 1Ω were realized by heating at temperatures between 550° and 720° C. The duration of the heating cycles was each time 1000 minutes.

The following table shows measured values of physical properties of carbon bodies manufactured according to the invention.

TABLE

| | |
|---|---|
| Bending (3) | 210 to 320 kg/cm$^2$ (1) |
| | 440 to 520 kg/cm$^2$ (2) |
| Pressure strength (3) | 1040 to 1430 kg/cm$^2$ (1) |
| | 1240 to 1830 kg/cm$^2$ (2) |
| Spec. el resistance | 12 to 16.10$^{-3}$ Ω cm |
| Permeability for air | 10$^{-2}$ to 10$^{-4}$ cm$^2$/s |
| | 10$^{-6}$ to 10$^{-7}$ cm$^2$/s |
| Density | 1.1 to 1.4 g/cm$^3$ |

(1) treated to 800° C.
(2) treated to 1600° C.
(3) The lower values of the strength apply to measurement at right angles to the lamination, the higher values to measurement parallel to the lamination.

Briefly, the particularities of this material in the carbonized state are as follows. The material has a porous variation of glassy carbon, in which during carbonization a primary porosity occurs from of the regular fabric structure and a secondary porosity of a less regular nature is formed by the fibrillary building up of the individual fabric fibers. This material is preferred and it can be processed both in the crude condition and in the carbonized state. The mechanical stability is so high that molded bodies of cuvettes having wall thicknesses of approximately 0.1 mm can be manufactured without particular difficulties. This results in the possibility of manufacturing cuvettes having a comparatively high electric resistance which achieves development of a "low power" cuvette. A specific electric resistance of approximately 12 to 16.10$^{-3}$ ohm.cm, which is high in comparison to graphite: approximately 1.5.10$^{-3}$ ohm.cm involves an increase of resistance by a factor of 10 to 100 due to possible reductions of the minimum wall thickness. A decisive advantage of the new material compared to compact glassy carbon consists in the carbonisation technique which can be carried out substantially more rapidly due to possible low wall thicknesses of, for example, 0.1 to 0.2 mm in conjunction with a porous structure.

The term "low power" cuvette is explained as follows. Due to the above-described properties of cuvettes of normal and spectrum graphite, respectively,—with or without a layer of pyrolytic graphite—rather bulky and hence expensive supply apparatus, for example transformers, is generally required for heating during analysis during which maximum temperatures of approximately 3000° C. are required. For example, the energy required for present day apparatus are partly 15 kW and higher. It is endeavoured to develop apparatuses operation with normal main voltages, such as for main voltages of 220 V with current strengths of at most approximately 25 A and power of approximately 5.5 kW. These values represent approximately the upper limit of a "low power" range. In other words, "low power" cuvettes are characterized by an overall resistance larger than or equal to $9\Omega$.

A disadvantage for use as an AAS cuvette is the porosity. Although the coefficient of permeability of $10^{-3}$ to $10^{-7}$ cm$^2$a$^{-1}$ is essentially lower than that of a very dense electrographite ($10°$ to $10^{-2}$ cm$^2$s$^{-1}$), a "sealing" of the basic material to suppress the memory effect is necessary. Therefore, an essential feature of the invention is that the cuvettes manufactured from the basic material are provided with an impermeable layer of carbon. In principle, two methods are possible for this purpose:

(a) the cuvette in the raw state is coated with a thin layer of a paint resin which is converted during carbonisation into a thin layer of substantially impermeable glassy carbon, (b) The carbonized cuvette is coated according to known methods with a thin layer of highly oriented pyrolytic graphite which is substantially impermeable up to the highest temperatures. Experience so far indicates that the latter aftertreatment apparently is the more effective one. It has further been found unexpectedly that as a result of this measure the overall resistance of the cuvette measured via the contacting at ends is noticeably increased. This increase in resistance is fully in line with the endeavoured "low power" cuvette.

The increase in resistance is determined by the crystallographic orientation of the layer of pyrolytic graphite as the contact faces. (The specific electric resistance of 2 to 5.$10^{-1}$ Ohm.cm of pyrolytic graphite at right angles to the layer is approximately a factor 10 larger than that of the basic material).

The advantages of the cuvettes according to the invention will be summarized again hereinafter:

The cuvette is a composite body which consists of a basic body of porous glassy carbon which is coated with a thin layer, in particular of pyrolytic graphite or also of dense glassy carbon.

A starting material for the basic body may be commercial laminated fabrics (see Saechtling-Zebrowski "Kunststoff Taschenbuch" 19th edition. Munich-Vienna 1074, pp. 417–419 and table 76).

The carbonisation times are very much shorter than in comparable bodies of resins without filters which result in compact glassy carbon.

The processing to a cuvette of a given geometry may be carried out with the starting material or also with the carbonized material using normal hard metal tools.

Due to the high rigidity, the cuvettes may be manufactured with very thin walls (thickness approximately 0.1 mm) in contrast with such cuvettes of graphite having thicknesses of approximately 0.5 to 1.0 mm.

In connection with the specific electric resistance which is comparatively high (1/10 of the resistance of graphite) cuvettes with a comparatively low current energy are hence possible.

On the basis of the available microporosity of the basic body, the enveloping carbon layer extends into the pores for a depth and as a result of this an extra-ordinary adhesion of the layer to the substrate material is achieved.

A few embodiments of the invention are shown in the drawing and will be described in detail hereinafter. In the drawing FIG. 1 is a sectional view of an AAS cuvette for horizontal operation.

Figure 1:
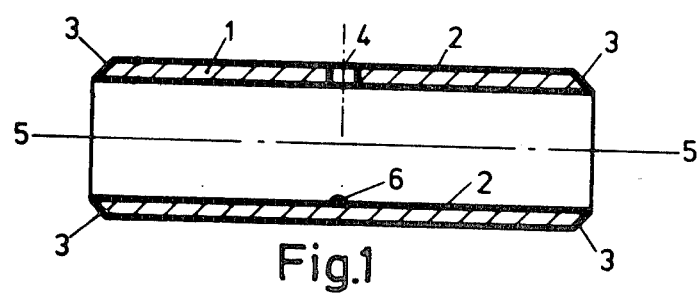
Figure 2:
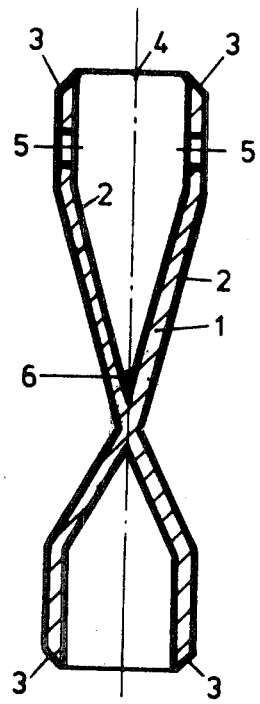
FIGS. 2a and 2b show two methods of processing bodies from the laminated compressed material.

FIG. 1a shows a sectional portion on an enlarged scale of the cuvette shown in FIG. 1, FIG. 2 is a sectional view of an AAS cuvette for vertical operation, FIG. 3 is a sectional view of a further AAS cuvette for vertical operation.

The cuvette shown in FIG. 1 consists of a basic body 1 of carbonized laminated fabric which is coated with an enveloping layer 2 of pyrolytic graphite. The coating layer is oriented so that the graphitic base planes preferably extend parallel to the surface of the basic body (FIG. 1a). As a result of this the porous basic body is sealed, and, protected from penetration of the analysis substance. Furthermore, a high heat insulation normal to the lamination as well as a considerable increase of the overall resistance of the cuvette measured between the contact faces 3 at the ends is achieved. The aperture 4 is provided in the wall and serves to fill the cuvette with the analysis substance. The measuring ray during operation passes through the cuvette along the line 5—5.

The material of the cuvettes shown in FIGS. 2 and 3 for vertical operation corresponds to that of the cuvette shown in FIG. 1. The filling aperture is each case the upper aperture 4. The measuring ray passes through the diameter of the cuvette through corresponding apertures along the line 5—5. Constriction resistances are formed by "constrictions" (X-shape, H-Shape). As a result of this, upon passage of current in the axial direction of the cuvette the site 6 on which the analysis probe is provided, is heated most strongly. The measuring apertures 5 are provides so that in this place the lowest possible temperature prevails. As a result of this, disturbing radiations are avoided.

What is claimed is:

1. A cuvette for flameless atom absorption spectroscopy comprising a cuvette basic body member being formed of a carbonized laminated fabric including cotton fabric and at least one of phenol resin or cresol resin, and a carbon layer formed on said basic body member.

2. A cuvette as claimed in claim 1, wherein said carbon layer is pyrolytic graphite.

3. A cuvette as claimed in claim 1, wherein said carbon layer is glassy carbon.

4. A cuvette as claimed in claim 1, wherein said cuvette basic body member has a shape providing a temperature distribution between a probe contained in said cuvette body member and measuring apertures of said body member.

5. A cuvette as claimed in claim 4, wherein said temperature distribution has a maximum at said probe and a minimum at said measuring apertures.

6. A cuvette as clamed in claim 4, wherein said basic body member has a constriction at which said probe is disposed, and said measuring apertures are spaced from said constriction.

7. A cuvette as claimed in claim 6, wherein said basic body member is cylindrical and said constriction has an X-shaped cross-section.

8. A cuvette as claimed in claim 6, wherein said basic body member is cylindrical and said constriction has a H-shaped cross-section.

* * * * *